United States Patent
Luotola et al.

(10) Patent No.: US 8,342,736 B2
(45) Date of Patent: Jan. 1, 2013

(54) SONICATION OF A MEDIUM

(75) Inventors: Juhani Luotola, Espoo (FI); Teuvo Sillanpää, Espoo (FI)

(73) Assignee: Orion Diagnostica Oy, Espoo (FI)

( * ) Notice: Subject to any disclaimer, the term of this patent is extended or adjusted under 35 U.S.C. 154(b) by 1225 days.

(21) Appl. No.: 11/919,732

(22) PCT Filed: May 5, 2006

(86) PCT No.: PCT/EP2006/004243
§ 371 (c)(1),
(2), (4) Date: Jun. 25, 2008

(87) PCT Pub. No.: WO2006/119932
PCT Pub. Date: Nov. 16, 2006

(65) Prior Publication Data
US 2008/0308404 A1    Dec. 18, 2008

(30) Foreign Application Priority Data

May 9, 2005    (GB) .................................. 0509418.0

(51) Int. Cl.
*B01F 11/02* (2006.01)
(52) U.S. Cl. ........ 366/110; 366/112; 366/114; 366/116; 366/127
(58) Field of Classification Search .......... 366/110–111, 366/112–113, 114–116, 127
See application file for complete search history.

(56) References Cited

U.S. PATENT DOCUMENTS

| | | |
|---|---|---|
| 4,198,461 A | 4/1980 | Keller et al. |
| 4,523,122 A | 6/1985 | Tone et al. |
| 4,571,087 A | 2/1986 | Ranney |
| 4,615,984 A | 10/1986 | Stoker |
| 5,160,870 A | 11/1992 | Carson et al. |
| 5,853,994 A | 12/1998 | Gopinathan et al. |
| 6,071,480 A * | 6/2000 | Halaka ........................... 422/128 |
| 6,086,821 A | 7/2000 | Lee |
| 6,368,553 B1 | 4/2002 | Lee |
| 6,686,195 B1 | 2/2004 | Colin et al. |
| 2003/0066915 A1 | 4/2003 | Taylor |

FOREIGN PATENT DOCUMENTS

| | | |
|---|---|---|
| EP | 1466966 A1 | 10/2004 |
| JP | 2001289831 A | 10/2001 |
| WO | WO 88/06927 A1 | 9/1988 |
| WO | WO-8806927 | 9/1988 |

OTHER PUBLICATIONS

International Search Report regarding Application No. PCT/EP2006/004243, mailed Aug. 23, 2006.
Japan Office Action regarding Application No. 2008-510467, mailed Jun. 27, 2011.

* cited by examiner

*Primary Examiner* — Yogendra Gupta
*Assistant Examiner* — Emmanuel S Luk
(74) *Attorney, Agent, or Firm* — Harness, Dickey & Pierce, P.L.C.

(57) ABSTRACT

Sonication of a medium for example in an immunassay is provided by applying sound waves from a transducer to a vessel in which the medium is held by a sonotrode coupled between the transducer and the vessel. The sonotrode has a recess in which the vessel is held, the recess being formed by facing surfaces of a plurality of protruding portions of the sonotrode separated by slits and arranged around the recess. The sonotrode is coupled to the vessel by dry contact with the vessel without any coupling layers therebetween. The use of such a sonotrode provides the advantages of allowing effective sonication with relatively low energy loss and with a low temperature elevation.

30 Claims, 6 Drawing Sheets

SONICATION OF A MEDIUM

The present invention relates to the sonication of a medium, particularly in a small in vitro diagnostics laboratory instrument, for example an immunoassay analyser or a clinical chemistry analyser.

Hereinafter, the term "sound" will be used to refer to both audible sound and ultrasound. Sonication is the application of sound waves. It is known to sonicate media for the purposes of performing reactions. Usually sonication is used to dissociate aggregates. A field of particular interest where sonication is used is in assays in which a sample is added to a reagent capable of detecting an analyte which might be present in the sample. Common types of assays are immunoassays. An example of the use of sonication in an immunoassay is for the purpose of mixing or to enhance production of aggregates, as for example in particle assisted assays. In most practical applications ultrasound frequencies (at least 20 kHz) are used, in which case the term ultrasonication may be used.

The most often used sonicator is a microtip sonicator probe which is applied into the medium to be sonicated. Alternatively, also large sonication baths are available. Sonication is usually only considered to be effective when the rod is surrounded by a liquid. This is on the basis that a solid contact between the transducer and the reaction vessel without any acoustic couplant material is generally considered not to transfer effectively the sound waves into the liquid medium inside the reaction vessel.

As acoustic waves fundamentally are mechanical vibrations, a medium is required for the waves to travel or propagate in. Vibrations on the surface of the sound source transfer the acoustic energy into the medium. To characterise a medium acoustically, the most important parameter is the acoustic impedance, Z. For a lossless medium, $Z=\rho c$, where $\rho$ is the density of the medium and c is the speed of sound in the medium. When the incident sound is perpendicular to the reflecting interface, i.e. when the angle of incidence is 0, the fraction of passed power $P_2$ and incident power $P_1$ is given by the formula:

$$P_2/P_1=(4Z_1Z_2)/(Z_1+Z_2)^2$$

In non-elastic media such as water and most liquids, there is continuous transition as long as the amplitude of the sound is relatively low. As amplitude is increased, however, the magnitude of the negative pressure in the areas of rarefaction eventually becomes sufficient to cause the liquid to fracture because of the negative pressure. This causes a phenomenon known as cavitation. Generally, below 100 kHz the intensity required to produce vaporous cavitation is almost independent of frequency. Above that, the intensity needed for vaporous cavitation rises as a function of frequency.

Available prior art documents disclose sonication applied using various techniques for various purposes, for example as follows.

U.S. Pat. No. 4,523,122 discloses an ultrasonic transducer and a one or two layer construction of an acoustic impedance matching layer formed on an ultrasonic wave-radiating surface.

U.S. Pat. No. 4,571,087 relates to a sonication apparatus for use in immunology, microbiology and clinical chemistry. Said patent provides an apparatus for rapid, automated sonication of a sample in the well of a microtiter tray, wherein the sonication energy is directed through an energy transmission medium along a defined propagation path.

U.S. Pat. No. 5,160,870 also discloses a composite layer which serves as a diaphragm underlying the transducer elements in addition to a micro-machinated ultrasonic sensing array having a plurality of piezoelectric transducers each of which generating an electric signal.

U.S. Pat. No. 5,853,994 relates to an improved particle agglutination assay system for determining one or more types of analytes by exploiting at least one class of finely divided polystyrene particles, each class having a predetermined narrow range of particle diameters. After produced conjugates between particles and the analyte present, the mixture is irradiated with bursts of ultrasound although the method of transmitting the ultrasound to the site of sample assaying is not described.

U.S. Pat. No. 6,368,553 and U.S. Pat. No. 6,086,821 (US-2002/0112541) discloses the use of ultrasonic force where the ultrasonic transducer is positioned either outside the reaction vessel where ultrasound is transmitted through a conduction medium or positioned so that it is submersed in the liquid of the reaction vessel. The patent family discloses a severe attenuation of the ultrasound when transmitted through the thick walls of a microtiter well or a microscope slide.

U.S. Pat. No. 4,615,984 discloses the application of ultrasound to a ligand-binder complex supported on a solid support to dissociate the ligand which may be employed in a solid phase assay. A sonic horn (a sonotrode) of the type commonly used in ultrasonic welding is used to transmit the ultrasound from a transducer to the medium containing the ligand-binder complex supported on a solid support. The document also suggests applying the ultrasound directly to the solid support to reduce the energy lost through the test tube wall and thereby to reduce the time and intensity of the ultrasound.

The teaching from the prior art discussed above is that the transducer without any acoustic couplant material does not transfer effectively produced sound energy into the liquid medium inside the reaction vessel. Usually a separate acoustic couplant material such as a liquid or gel-like material is used for this purpose. Accordingly, said applications demand an efficient acoustic coupling between the transducer and sonicator probe and the material to be sonicated. Rubber-like materials also have been developed especially for the field of non-destructive testing (NDT). Aqualene™ from R/D Tech is one example of elastomeric couplants which are especially suitable for NDT purposes. Medical applications utilise mostly gel-like compounds with very high water content for acoustic coupling of transducers to the human body.

There are also known large sonication baths in which transducer has a fixed coupling with the container. A couplant material may be used. Epoxy or acrylic glues are often used for this purpose. WO-88/06927 discloses such a large sonication bath configured for silent operation and in which a conical part of the transducer is coupled to the bath container.

US-2003/0066915 discloses a sonication apparatus for disrupting cells or viruses by holding them in the convex recess of a dome shaped wall. The wall is sufficiently elastic to permit deflections in response to the vibrations from the sonotrode. A sonotrode coupled to a transducer contacts the wall under a preload force sufficient to stress the wall. The elastic constant of the wall and the preload force are chosen to adjust the natural frequency of the wall to be equal to the operating frequency of the transducer.

U.S. Pat. No. 4,198,461 discloses the preparation of polymeric fibers and masses by precipitation from solution in a sonication apparatus. The solution is held in a container within a holder mounted on a shaft driven by a shakerhead at frequencies of from 80 Hz to 2000 Hz.

U.S. Pat. No. 6,686,195 and EP-1,466,966 disclose a sonication apparatus for sonicating a biological sample to lyse cells within the sample. The sample is held in a test tube having a rounded end. A sonotrode is coupled between a transducer and the test tube. The sonotrode has a concave recess shaped to fit the rounded end of the test tube to improve the efficiency by contacting a larger area of the test tube than an apparatus in which the test tube is placed on the tip of a sonotrode.

Whilst some of the known sonication apparatuses are effective in sonication a medium, it remains desirable to effect sonication of a medium with low energy losses and low temperature elevation.

According to a first aspect of the present invention, there is provided an apparatus for sonicating a medium comprising:
a vessel for holding the medium;
a transducer operable to produce sound waves; and
a sonotrode coupled to the transducer, the sonotrode comprising a plurality of protruding portions separated by slits, the plurality of protruding portions being arranged to mechanically hold the vessel.

According to a second aspect of the present invention, there is provided a method of sonicating a medium using such an apparatus.

Thus, sonication of a medium is provided by applying sound waves from a transducer to a vessel via a sonotrode coupled between the transducer and the vessel. The particular design of the sonotrode has been found to be effective in sonicating a medium with a relatively energy loss and with a relatively low temperature elevation. This is understood to be achieved as follows. The sonotrode has a plurality of protruding portions separated by slits which hold the vessel. For example in the simplest design there are two protruding portions separated by a single slit. In this design, each of the protruding portions vibrates in a flexing mode and transmits vibrations to the vessel, much like the vibrations of a tuning fork. Thus the design of the sonotrode is effective in transmitting vibrations to the vessel. For example, the combination of the vessel and the sonotrode may be caused to resonate. As a result the vibrations cause the whole vessel to vibrate with a large flexural amplitude, thereby being effective in transmitting vibrations to the medium in the vessel. This may be thought of as increasing the energy transmitting area from merely the contact area.

The design of the sonotrode has particular advantage when used in applications of sonication where cavitation of the medium is desired. In this case, the design of the sonotrode allows the cavitation level to be easily controlled.

Furthermore the invention may be applied relatively cheaply, thereby allowing wide application. One field of application is in small in vitro diagnostics laboratory instruments, for example an immunoassay analyser or a clinical chemistry analyser. In this case the medium typically contains an assay reagent capable of detecting an analyte. It is possible to utilise the invention in combination with existing analyser technology or with future technology, e.g. for future low cost in vitro diagnostic platforms enabling the use of ultrasound and real time kinetic measurements without disturbing heat generation inside the test vessel.

Accordingly, the sonication apparatus of the present invention can be utilised as an integrated elementary part of an immunological or clinical chemistry analyser for disintegrating the sample material (e.g. for breaking the bonds between aggregates and for cell disruption, hemolysis, homogenisation), for mixing the sample material with other reagents needed for specific analysis and for enhancing the reaction kinetics. Being an integrated part of the analysis system (e.g. an optical block) this sonication apparatus enables accurate kinetic measurements to be made. Additionally, because of the efficiency in sonic energy transport from the transducer into the liquid inside a measurement vessel or cuvette this system allows very low power consumption, making it suitable for battery powered device.

Similarly, the invention is suitable for in vitro diagnostic tests as point of care (POC) and point of use (POU) type applications. Moreover, the insertion and removal of test vessels without any acoustic couplant in the sonication system is easy and reproducible and can be directly coupled to the mechanics and electronics especially designed for this sonication system.

Furthermore, this system can adapt different volumes and physico-chemical (e.g. densities, temperatures, suspensions, dispersions, physical environmental changes) characteristics of liquids inside said vessel. It can be part of the optical cuvette chamber construction by enabling simultaneous mixing, disintegration, separation and enrichment functions and the real time optical follow up of the reactions and temperature changes taking place inside the vessel. Controlling the real time mixing and temperatures enables very exact timing of the kinetic reactions inside the measurement vessels cuvette of the analyser. This kind of accurate kinetic timing after and before sonication have not been possible earlier in analysers available on the market as e.g. in particle assisted immunoassays.

In general the sonication may have any purpose including but not limited to sample and reagent processing; dissociation; vaporous cavitation; mass transfer; disintegration; mixing; reaction enhancement; enrichment or separation of reagents or analytes; reaction control with timing; reaction control with temperature; reaction control with kinetic energy; and reaction control with the reactions typical for sonochemistry. One particularly advantageous application of the sonication is in the technique disclosed in the International Patent Application being filed simultaneously with this application entitled "Measurement Of Binding Rate Of A Binding Substance And An Analyte" and claiming priority from British Patent Application No. 0509419.8. A further benefit of the invention is that it allows the integration of multiple immunoassay components and the sample resulting in a homogenous assay in order to achieve disruption of bindings and aggregates, and mixing thereof so enabling measurement of the initial rate of binding reaction.

Depending on the application, the medium may be of any type. Some examples are now given but these are not limitative. The medium may be a solution or a suspension, for example comprising particles, ligands or anti-ligands in a fluid. The method may be used for measuring a single or multiple analytes and kinetics thereof. The particles used in an assay may have different size and composition (as polymer materials, silica, colloidal gold and magnetic etc.). Moreover, liposomes, cells, microorganisms etc. can also be used. Additionally the described invention is amenable to the simultaneous measurement of several analytes using for example photometric, fluorometric and magnetometric means, wherein the size of each individual group of the aggregates are identifiable by the size and characteristics of the particle being involved in formation of said aggregate.

Both clinical and non-clinical, such as hygiene samples, can be analysed utilising the present invention. Samples from different body fluids such as whole blood, serum, plasma, spinal fluid, ascites fluid, urine, saliva, semen and samples for hygiene monitoring such as food, milk, sterility control swipes from surfaces or water can be used.

Usually the analyte is determined from the sample without any additional processing, however, if needed the sample may be pre-treated prior to the assay, e.g. centrifuged, haemolysed or enriched.

The vessel may be of any type, for example a test tube, cuvette, or a vial. The vessel can be removable which is advantageous for handling of the medium and reuse of the apparatus. An alternative is for the vessel to be fixed to the sonotrode.

Any sonication frequency, amplitude and time may be used in accordance with the purpose of the sonication.

The frequency is usually at least 1 kHz, but more typically at least 20 kHz in which case frequency may be termed ultrasonication. Particular advantage is achieved where the frequency is at least 35 kHz. Usually, the frequency is at most 10 MHz, more typically at most 1000 kHz or at most 100 kHz or at most 50 kHz, but the frequency is not limited thereto. For typical applications, the resonant frequency will be in the range from 20 kHz to 100 kHz.

The method and apparatus is particularly suited to relatively low energies, for example in which the power of the sound waves supplied to the medium 8 is 10 W or less, 8 W or less, or 5 W or less, but the power is not limited thereto and could be greater than 10 W. These powers apply to a volume of the medium 8 of 0.1 ml to 2 ml, for example. For other volumes, the powers might be adjusted pro rata.

The amplitude of the oscillations in the medium is dependent on the energy of the absorbed sound waves. The method and apparatus is particularly suited to amplitudes of oscillations in the medium of at most 100 µm, at most 75 µm or less, or at most 50 µm. Typically, the amplitudes of the oscillations in the medium will be at least 10 µm, at least 25 µm or at least 50 µm.

Similarly, the sound waves may be formed as appropriate for the purpose of the sonication. For example the sound waves may be continuous or may be provided in one or more pulses. The sonication is applied for a period sufficiently long to carry out the intended purpose, this typically being of the order of seconds.

Preferably, the design of the sonotrode and the frequency of the sound waves are selected in dependence on each other so the sound waves cause the combination of the sonotrode and the vessel to resonate. Such resonance assists the efficient application of sound waves to the medium. Thus for efficient sonication, the design and mechanical dimensions of the sonotrode can be changed when the sonication frequency is changed.

Furthermore, the contact may be dry and without any coupling layers so there is no extra conduction medium acting as an acoustic couplant between the sonotrode and the vessel.

To allow better understanding, an embodiment of the present invention will now be described by way of non-limitative example with reference to the accompanying drawings, in which.

Figure 1:
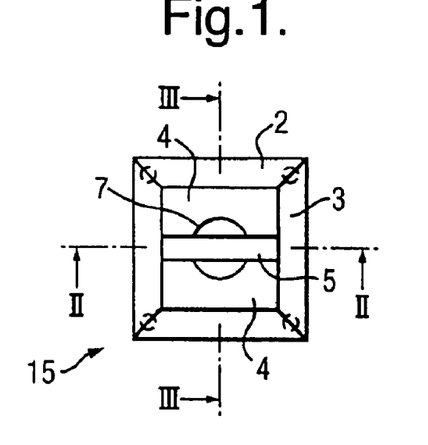
FIG. 1 is a top view of a sonication apparatus.
Figure 2:
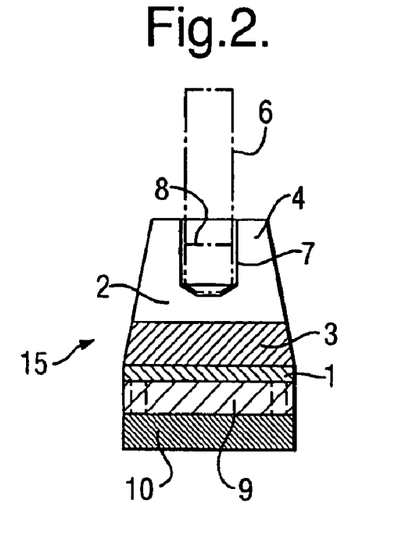
FIG. 2 is a cross-sectional view of the sonication apparatus, taken along line II-II in FIG. 1.
Figure 3:
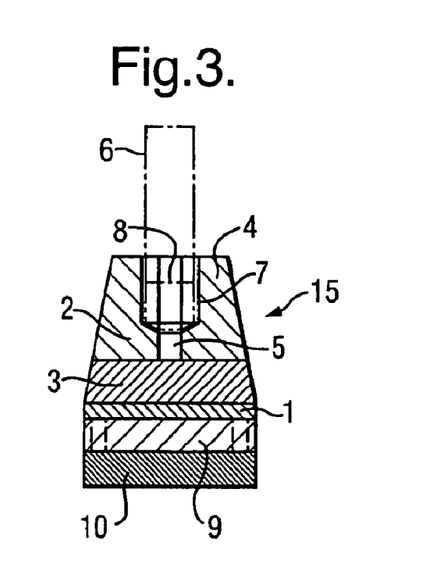
FIG. 3 is a cross-sectional view of the sonication apparatus, taken along line III-III in FIG. 1.

The mechanical construction of the sonication apparatus 15 is shown in FIGS. 1 to 3.

The sonication apparatus 15 has a piezoelectric transducer 1 which is operable to produce sound waves. The transducer 1 is coupled directly to a sonotrode 2 which is formed as single piece of material, preferably aluminum which is cost-effective and easy to manufacture. Thus sound waves produced by the transducer 1 are transferred through the sonotrode 2.

The sonotrode 2 has a construction with a general arrangement similar to that of a tuning fork. In particular, the sonotrode 2 comprises a base portion 3 which is coupled to the transducer 1 and from which two protruding portions 4 protrude on the opposite side from the transducer 2, generally the uppermost side in use. The protruding portions 4 are separated by a slit 5. The protruding portions in this design are identical and thus have the same vibrational modes. The protruding portions 4 have a length which is of the order of, or more preferably equal to, a quarter of the wavelength of the sound waves produced by the transducer 1 in normal operation as they propagate in the material of the protruding portions 4. As a result, the vibration of the protruding portions 4 resonates at a frequency close to the sound waves with which they are driven.

The sonotrode 2 holds a cuvette 6 (shown in dotted outline in FIGS. 2 and 3) between the protruding portions 4. This is achieved by the protruding portions 4 having a recess 7 formed between the protruding portions 4, that is the recess 7 being formed by facing surfaces of each of the protruding portions 4. The recess 7 is shaped to conform with the cuvette 6. In this case the cuvette 6 has a circular cross-section and so the recess 7 also has a circular cross section, but in general the cuvette 6 and recess 7 could have a different shape such that the recess 7 formed by facing surfaces of each of the protruding portions 4 has a correspondingly different shape. Thus the recess 7 mechanically holds the cuvette 6 by friction.

To increase the frictional force the recess 7 may be designed with slightly smaller dimensions than the outer dimensions of the cuvette 6. In this case, the protruding portions 4 may be forced outwardly during insertion of the cuvette 6 into the recess 7 and subsequently released.

Although in this example the sonotrode 2 mechanically holds the cuvette 6 by friction, other types of mechanical couplings could be equally provided, for example a screw fitting.

The contact between the sonotrode 2 and the cuvette 6 is dry and without any coupling layers or other medium acting as an acoustic couplant. The ability to avoid a couplant is a particular advantage of the apparatus 1, although in principle such a couplant could be used.

The cuvette 6 is an elementary and interchangeable part of the sonotrode 2. In use the cuvette 6 and sonotrode 2 vibrate together at the resonant frequency of the combination. The cuvette 6 and the sonotrode 2 are designed to have a resonant frequency suitable for a desired application of the sonication. For example, an actual sonication apparatus 1S with which measurements have been taken has a resonant frequency of 40 kHz and is driven at 37 kHz. The sonication apparatus may alternatively be arranged to have a higher resonant frequency of for example 60 kHz. Use of a higher resonant frequency has the advantages of reducing noise and providing smaller mechanical dimensions.

Figure 4:
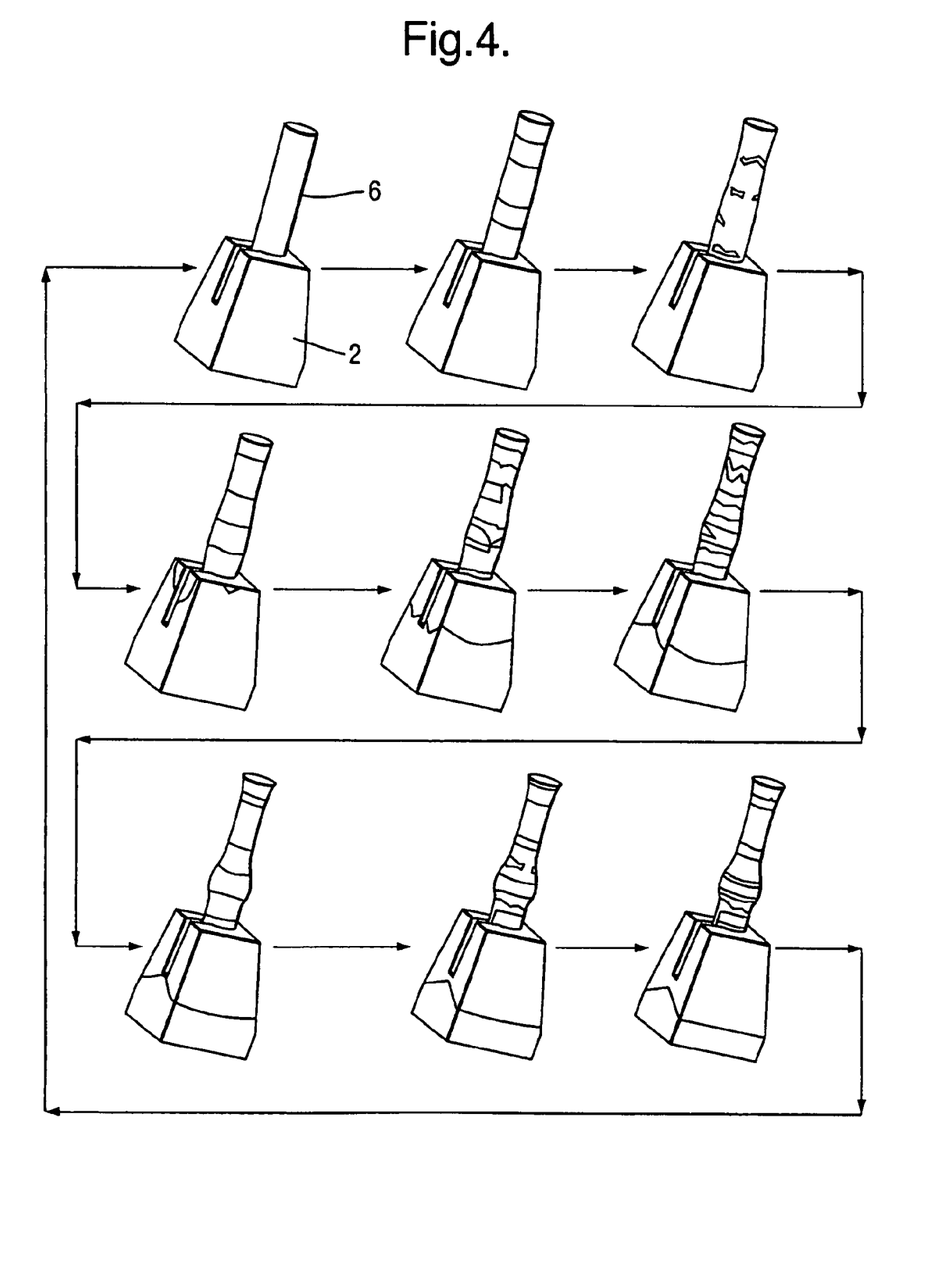
FIG. 4 shows a computer simulation (ANSYS) of the resonance phenomenon in the sonication apparatus.

In operation the sound waves produced by the transducer 2 are transmitted by the sonotrode 2 to the cuvette 6. In use, the cuvette 6 holds a medium 8 and the sound waves are transmitted through the cuvette 6 to that medium 8. For example, FIG. 4 shows a computer simulation (ANSYS) of operation of the sonotrode 2 and the cuvette 6 in the sonication apparatus 15. It is evident that the cuvette 6 acts as a fundamental resonating part of the combination with the sonotrode 2. The ultrasonic energy of 44 kHz moves from the sonotrode 2 through and along the cuvette 6 into the medium 8 inside the cuvette 6, thereby causing sonication of the medium 8.

The shape of the sonotrode 2 with a slit 5 between the protruding portions 4 is advantageous in establishing and controlling the resonant vibration of the sonotrode 2 and in thus transmitting sound waves to the cuvette 6. To facilitate this the recess 7 extends to a lesser depth than the slit 5 so that the cuvette 6 is held solely by the protruding portions 4, although this is not essential and a similar effect could be achieved if the recess 7 extends to a greater depth than the slit 5.

The slit 5 also has the advantage of enabling the passage of light which is useful in many applications where it is desirable to monitor optically a reaction inside the cuvette 6.

The geometry of the sonotrode 2 also enables other useful acoustical modes.

Although the design of the sonotrode 2 employs two protruding portions 4, in general the sonotrode could employ any plural number of protruding portions 4 arranged around the recess 7 and the principle of operation would be the same.

The sonication apparatus 15 has a mounting arrangement as follows. The transducer 1 is supported by a backing mass 9. The backing mass 9 provides a reaction to the sound waves generated by the transducer 1 and is formed simply as a block of material such as aluminum, but could in general have a more complicated construction. Bolts 11 between the sonotrode 2 and the backing mass 9 provide compression of the transducer 1 against the sonotrode 2 for effective transfer of sound waves.

The backing mass 9 is supported by a damper 10 for isolation of the transducer 1 from the surface on which it is seated. The damper 10 may be formed simply as a block of material such as rubber, but could again have a more complicated construction.

There will now be described some alternative constructions for the sonication apparatus 15 which employ different arrangements for mechanically holding the cuvette 6 on the sonotrode 2.

Figure 5:
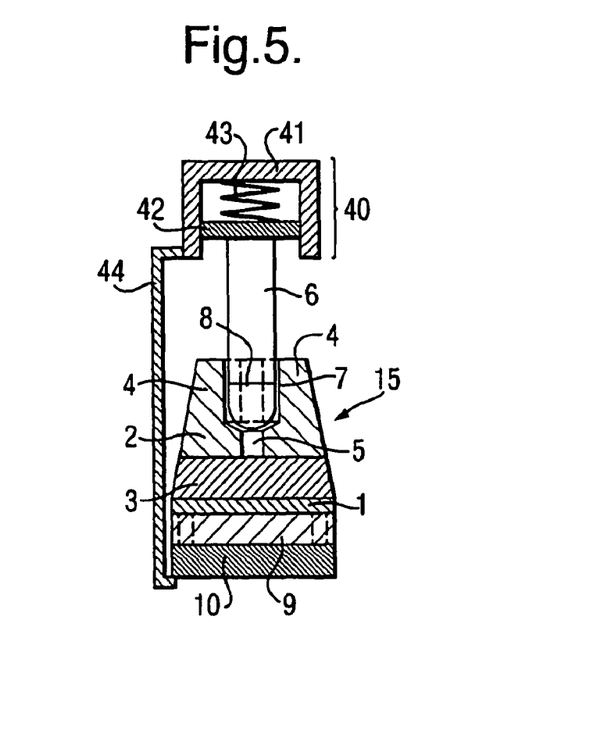
FIG. 5 is a cross-sectional view of the sonication apparatus with a first alternative construction, taken along line II-II in FIG. 1.

A first alternative construction for the sonication apparatus 15 is shown in FIG. 5 which is a cross-sectional view similar to that of FIG. 3. In this alternative construction, the sonication apparatus 15 is modified by additional providing a loading arrangement 40 which loads the cuvette 6 against the sonotrode 2. In particular, the loading arrangement 40 comprises a housing 41 housing a movable plate 42 and a spring 43 which biases the plate 42 away from the housing 41. The loading arrangement 40 is mounted with the plate 42 engaging the upper end of the cuvette 6 and with the housing fixed relative to the remainder of the sonication apparatus 15, in this example by a plurality or arms 44 (one of which is shown) extending from the housing 41 to the damper 10, or alternatively to another part of the sonication apparatus 15. Instead of the arms 44, the loading arrangement 40 could be held relative to the sonication apparatus 15 in any other way, for example by arranging the sonication apparatus 15 and the loading arrangement 40 in a box which when closed holds them together.

Thus the action of the bias spring 43 loads the cuvette 6 against the sonotrode 2. The loading arrangement 40 is arranged to minimize any vibration thereof and in particular to not resonate with the cuvette 6.

The advantage of the loading arrangement 40 is to improve the transmission of vibrations from the sonotrode 2 to the cuvette 6. It also reduces the coupling force needed to be applied directly between the sonotrode 2 and the cuvette 6, for example requiring the recess 7 to provide a less tight fit.

The loading force of the bias spring 43 is selected to provide a sufficient degree of coupling between the sonotrode 2 and the cuvette 6 to enable a proper conduction of vibrations. The force is typically in the range of 1N to 40N, for example about 20N.

The loading arrangement 40 is advantageously arranged to transmit the loading force to the cuvette 6 at a point of minimal flexural vibration of the cuvette 6, ie at a nodal point of the vibration. This may be achieved by design of the relative values of the length of the cuvette 6 and the resonant frequency of the combination of the cuvette 6 and the sonotrode 2. There may be multiple points of minimal flexural vibration along the cuvette 6 and loading could alternatively be applied at any or all of such points. Transmitting the loading force to the cuvette 6 at a point of minimal flexural vibration of the cuvette 6 has the advantage of providing a minimal damping effect on the vibration of the cuvette 6.

The loading arrangement 40 is one example of how the cuvette 6 can be loaded against the sonotrode 2. Such loading may be achieved in other ways. Also, the cuvette 6 may be provided with protrusions on which loading can be applied. The load is not necessarily applied on the end surface of the cuvette 6 and could alternatively be applied on a side surface of the cuvette 6. Loads may be applied in more than one location. The load can be applied by techniques other than a spring. One of several alternatives is to arrange the sonication apparatus 15 in a box with a tightly fitting lid which loads the cuvette 6 against the sonotrode 2

Figure 6:
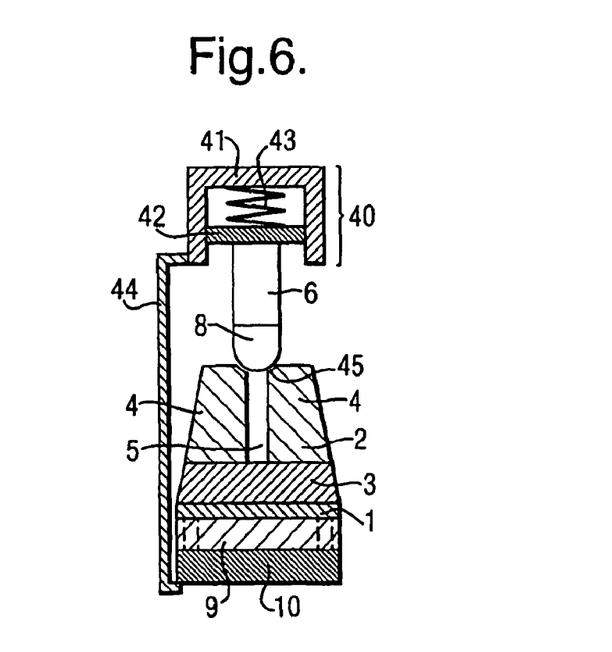
FIG. 6 is a cross-sectional view of the sonication apparatus with a second alternative construction, taken along line II-II in FIG. 1.

A second alternative construction for the sonication apparatus 15 is shown in FIG. 6 which is a cross-sectional view similar to that of FIGS. 3 and 5. In this alternative construction, the sonication apparatus 15 is modified as compared to the first alternative construction as follows. The protruding portions 4 of the sonotrode 2 are formed without a recess 7. Instead, the protruding portions 4 are arranged to mechanically hold the vessel on their outer ends 45. The outer ends 45 are shaped to conform with the lower surface of the cuvette 6 and the cuvette 6 is loaded against the outer ends 45 by the loading arrangement. The outer ends 45 have a concave shape which thus serves to centre the cuvette 6 on the protruding portions 4, but alternatively the outer ends 45 could be planar.

As a further alternative, the second alternative construction of FIG. 6 could be modified by omitting the loading arrangement and instead mechanically holding the cuvette 6 on the outer ends of the protruding portions 4 by a mechanical coupling.

Figure 7:
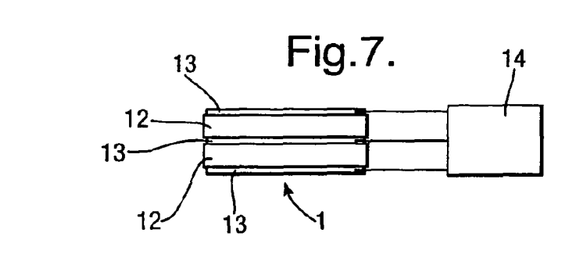
FIG. 7 is a schematic view of the transducer and drive circuit of the sonication apparatus.

The construction of the transducer 1 and the electrical elements of the sonication apparatus 15 are shown in FIG. 7.

The transducer 1 has a conventional bimorph bender construction consisting of a stack of two layers 12 of piezoelectric material alternating with electrodes 13. In general the transducer may have any construction capable of generating the desired sound waves but a typical example will be a product manufactured by the company Ferroperm. Typically the layers 12 of piezoelectric material will be disc shaped and the transducer might have a diameter of 30 mm and a thickness of 2 mm. The piezoelectric material may be a ceramic such as PZT, for example PZT 26 having an acoustic impedance Z of 2.70E+07 kg/(m²/s).

A drive circuit 14 supplies a drive signal to activate the transducer 1. The drive signal is applied to the electrodes 13. The polarity of the drive signal and the polarity of the layers 12 of piezoelectric material are chosen so that the layers 12 of piezoelectric material undergo differential change in length with one expanding while the other contracts. This differential change in length causes bending of the transducer which generates sound waves. Other forms of transducer could be used to similar effect.

The materials of the cuvette 6 and sonotrode 2 the overall design of the sonotrode 2 are chosen based on a consideration of the transmission of sound waves from the transducer 1 to the medium 8. To achieve an efficient narrowband transmission from the transducer 1 to the cuvette 6, it is desirable for the acoustic impedance $Z_2$ of the sonotrode 2 to equal to the "geometric mean" ($Z_2=\sqrt{(Z_1Z_3)}$) of the acoustic impedance $Z_1$ of the transducer 1 and the acoustic impedance $Z_3$ of the cuvette 6, or close thereto (say within 50% of the geometric mean). One advantageous combination of materials is for the transducer 1 to be made from PZT 26 having an acoustic impedance $Z_1$ of 2.70E+07 kg/(m²/s), the sonotrode 2 to be made from aluminum having an acoustic impedance $Z_2$ of 1.70E+07 kg/(m²/s) and the cuvette 6 to be made from Ticona Topas 8007® having an acoustic impedance $Z_3$ of 1.65E+06 kg/(m²/s). For comparison, water has Z value of 1.50E+06 kg/(m²/s) and air has Z value of 4.10E+02 kg/(m²/s).

Another consideration is to form the cuvette 6 from a material having an acoustic impedance providing acoustic matching between the sonotrode 2 and the medium 8. The combination of materials mentioned above meets this requirement, in particular providing a matching of at least 0.4 times the optimum matching, this being adequate matching for a battery operated device. Thus in narrowband an efficient sound transmission to the cuvette 6 was achieved. Other materials for the cuvette 6 were considered, but Ticona Topas 8007® had the optimal acoustic impedance and mechanical characteristics of the materials considered. Accordingly, there is extremely good transmission of sound waves from the transducer 1 to the medium 8.

Furthermore Ticona Topas 8007® has the advantage of providing a low energy loss due to internal friction. As the cuvette 6 resonates in combination with the sonotrode 2 this improves the efficiency of the operation of the sonication apparatus 15.

Similar advantages may be achieved with other thermoplastic olefin polymers of amorphous structure, of which Ticona Topas 8007® is an example. For example, the material of the cuvette 6 may be a cyclic olefin copolymer (COC). Such polymers are copolymers of ethylene and a ring-structured olefin, typically derived from dicyclopentadiene. The incorporated ring structure gives COCs their stiffness, while its size prevents the molecules from becoming ordered enough to crystallize. The nature of these polymers is completely amorphous, resulting in parts with low shrinkage and warpage. These features make COC materials especially applicable for ultrasound usage for example for vessels or cuvettes used in in vitro diagnostic instrumentation.

However, in general the cuvette 6 could be made from other plastic materials such as polypropylene, polyethylene, polymethylpentene and polystyrene may also be used, although they may not be as suitable and efficient for transmission of the sound energy into the reaction vial as the material used in the present invention. Similarly, any other material, for example plastics, glass, quartz, silicon and metals, is suitable as long as it provides a sufficiently good matching impedance and resonator properties.

Figure 8:
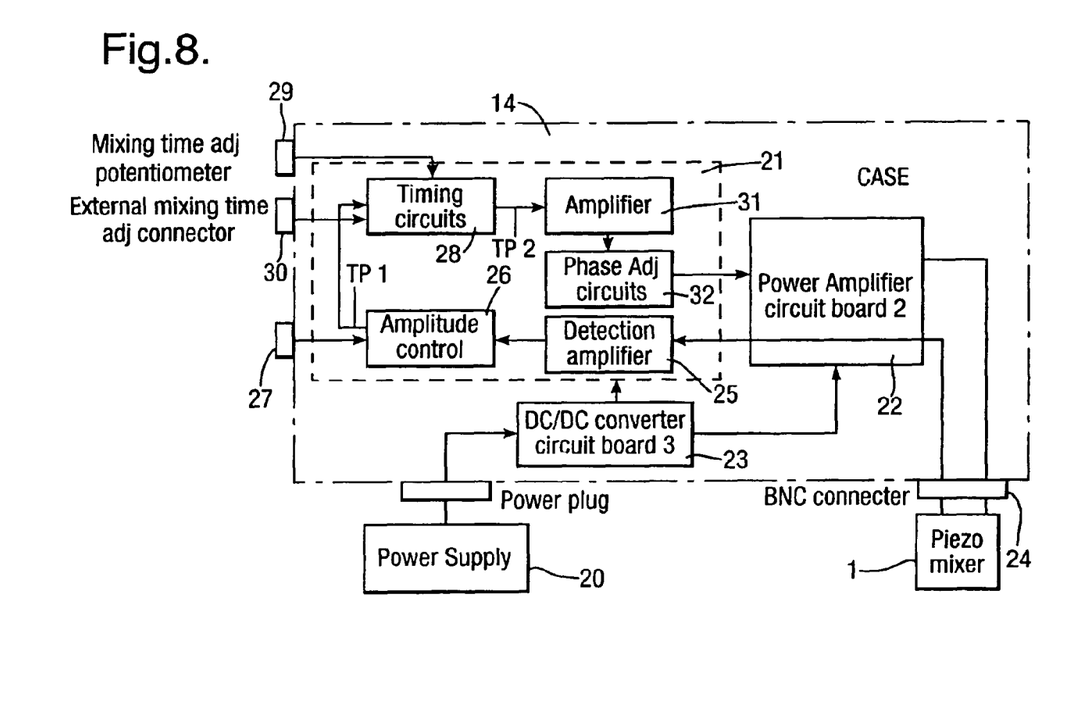
FIG. 8 is a circuit diagram of the drive circuit.

The drive circuit 14 is illustrated in FIG. 8 and will now be described.

The drive circuit 14 is reasonably simple and finds the proper operating frequency regardless of the volume of the medium 8 in the cuvette 6. The drive circuit 14 is powered by a battery 20 and consists of three circuit blocks, namely:

a control block 21, which includes mixing time control, amplitude control, phase adjust circuits and detection circuits, and which generates a drive signal in the correct form;

an amplifier block 22 which amplifies the drive signal from the control block 21 and supplying it to the transducer via a BNC connector 24; and a DC power block which performs DC/DC conversion of the voltage from the battery and supplies power to the control block 21 and the amplifier block 22.

The control block 21 comprises tracking electronics, and sonication time and amplitude controls, as follows.

A detection amplifier 25 measures current flowing through the transducer 1.

An amplitude control block 26 controls the oscillation amplitude to be related to the sonication power, based on the output of the detection amplifier 25. The amplitude control block 26 may be set by an amplitude potentiometer 27.

A timing circuit 28 receives the output of the amplitude control block 26 and closes the feedback loop, thus enabling free oscillation. The mixing time is controlled by FET-switch which enables the feedback circuit. The loop closing time of the timing circuit 28 is set by a timer potentiometer 29 or an input from a mixing time adjustment connector 30.

The output of the timing circuit 28 is supplied to an amplifier 31 which sets correct gain and buffers the feedback signal.

The output of the amplifier 31 is supplied to a phase adjustment circuit 32 which sets the correct phase to feedback signal.

The operation of transducer 1 and the rest of the sonication apparatus 15 is based on a free oscillation. In free oscillation, the combination of the backing mass 9, the transducer 1, the sonotrode 2 and the cuvette 6 is used as a "tank circuit" which determines the oscillation frequency of the system.

Figure 10:
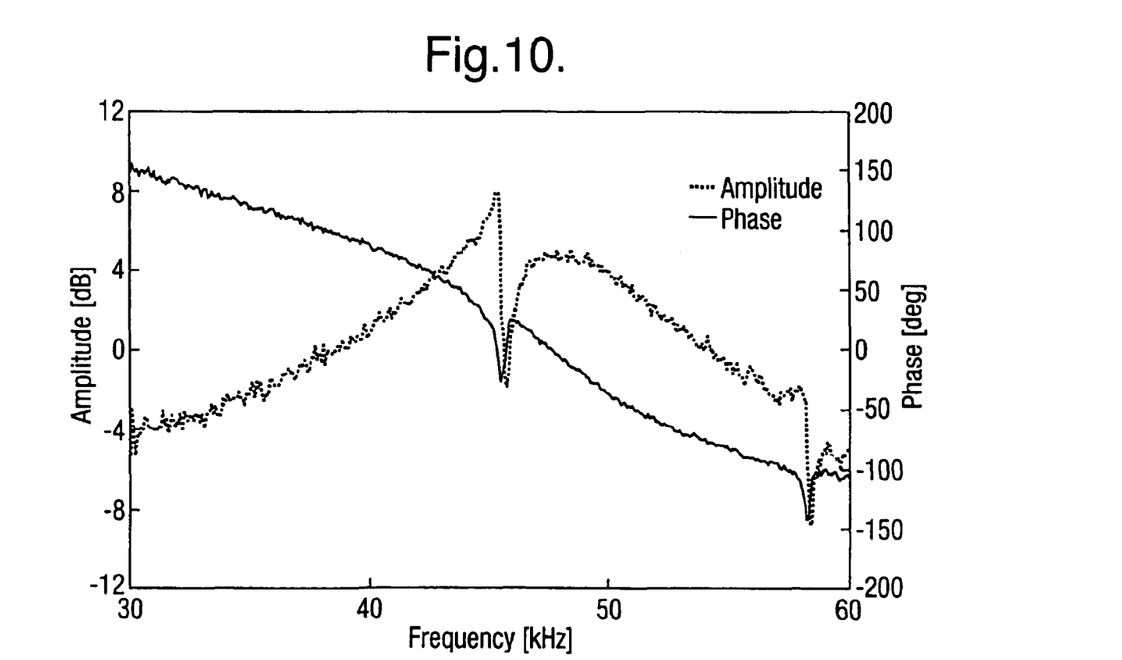
FIG. 10 is a graph of the loop response of the sonication apparatus.

The amplifier block 22 generates a high voltage using a power amplifier and ferrite core transformer. The maximum output voltage from the power amplifier is +10V to −10V and the maximum output voltage from the transformer is 400 Vpp (peak to peak). The high voltage is driven into the transducer 1 and the current is measured. The output voltage of detection amplifier 25 is relative to the current flowing through the "tank circuit". This voltage is fed backed to the power amplifier of the amplifier block 22 as described above. If the feedback voltage and drive voltage are in same phase and the open loop gain of the system is $\geq 1$ the circuit starts to oscillate in the frequency where these boundary conditions are fulfilled. The open loop response measured from TP1 to TP2 (the input and output of the timing circuit 28) is shown graphically in FIG. 10. The response is measured by transmitting random noise to the TP1 and measuring the response from TP2. The gain and phase fulfils the free-oscillation boundary conditions. In the control electronics, an LC-band pass filter is used to achieve right kind of shape to the phase response and for limiting the bandwidth. The center frequency of the LC-filter must be approximately same as the resonance frequency of the sonication apparatus 15. The power of the circuit can be adjusted by limiting the detection amplitude at the detection amplifier 25, for example using adjustable diode limiters.

Figure 9:
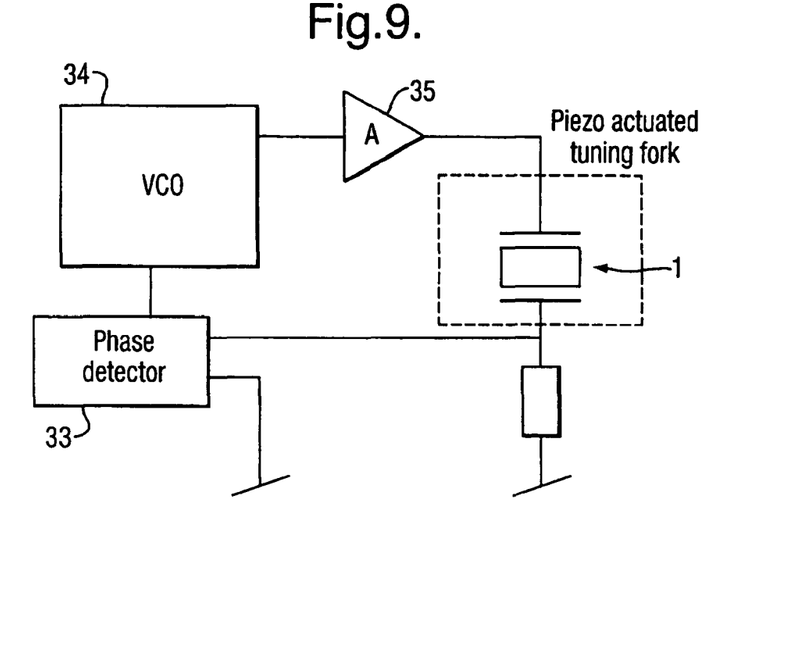
FIG. 9 is a schematic diagram of a phase locked loop (PLL) realisation in the drive circuit.

As an alternative to free oscillation, forced oscillation could be used. In this alternative, a phase locked loop (PLL) is used to find the right operation frequency automatically as shown schematically in FIG. 9. In particular, at the resonance the phase of the actuating AC-current over the transducer 1 changes. In the PLL the phase of the actuating current is measured by a phase detector 33. The voltage relative to the phase is directed to a voltage controlled oscillator (VCO) 34 which produces an oscillatory drive signal supplied via an amplifier 35 to the transducer 1. If the resonance frequency of the sonication apparatus 15 changes, the output voltage of the phase detector 33 also changes. This voltage controls the oscillation frequency of the VCO 34 in a way that the phase detector 34 output voltage stays at the predetermined value. In this way the frequency tracks the new resonance. If the resonance frequency of the sonication apparatus 15 changes, also the output voltage of the phase detector 33 changes.

An optional feature is tuning of the sonication apparatus 15, either manually or automatically, in order to find the optimal amplitude and phase which enables an efficient transfer of energy from sonotrode 2 to the cuvette 6, despite of the material of the cuvette 6 chosen for the assay.

An additional option of the sonicator is the possibility to switch from high to low energy sonication state either manually or automatically. Taking into account different geometric requirements it is also possible to exploit standing wave type sonication.

Figure 11:
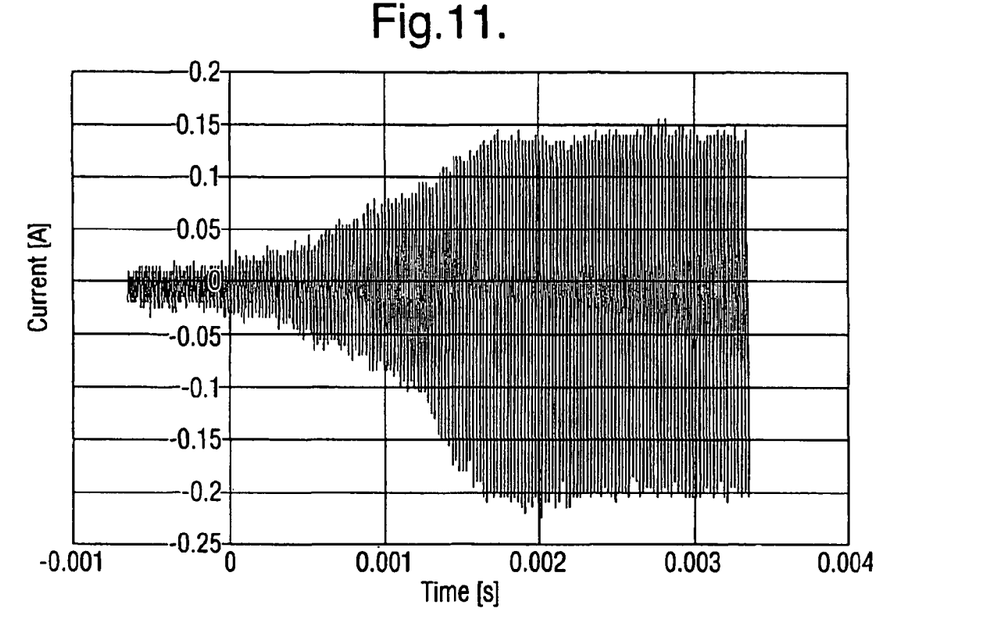
FIG. 11 is a graph of the current through the transducer.
Figure 12:
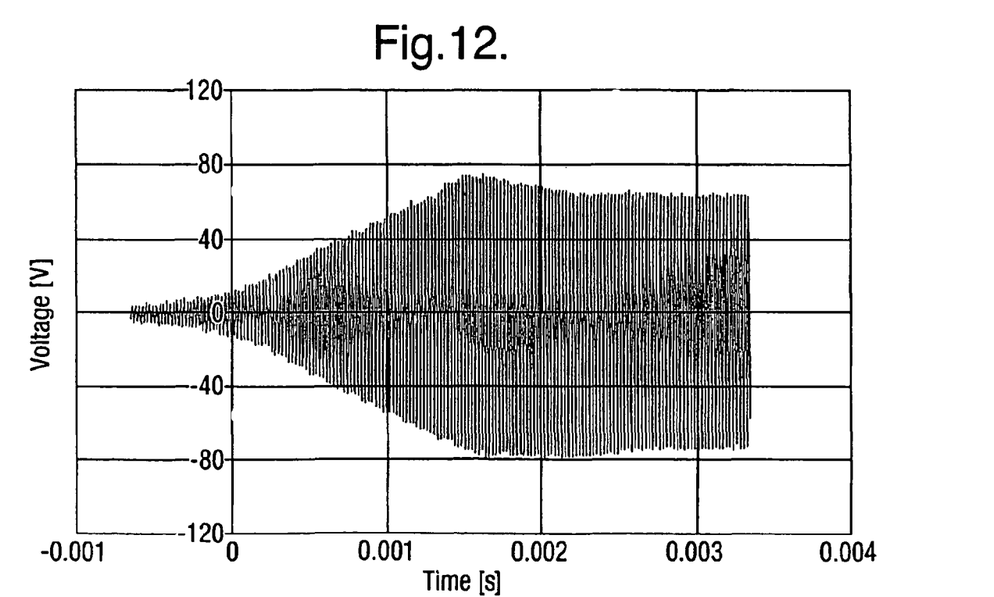
FIG. 12 is a graph of the voltage across the transducer.

The sonication apparatus 15 enables much lower energy, heat and audible noise generation for excellent ultrasonication at the frequency of about 40 kHz than available methods usually utilising the frequency around 20 to 25 kHz. To illustrate this, FIGS. 11 and 12 show the variation in current and voltage, respectively, at the transducer 1 over time. FIG. 11 shows that the amount of current through the transducer 1 is between 100-300 mApp, with the power control in minimum position i.e. ~70% of maximum power. FIG. 12 shows that the amount of voltage over the piezo elements during sonication procedure was 120-160 Vpp. The instantaneous power consumption of the mixer part at minimum power is thus approximately 14 W (average 7 W).

The power of the sound waves supplied to the medium 8 is estimated to be around 4 W with 1.0 ml of the medium 8. The power consumption by the drive circuit 14 is estimated to be around 25 W. On the basis of these estimates, the efficiency is approximately 16%.

The sonication apparatus 15 has been developed to sonicate a medium as part of the technique disclosed in the International Patent Application being filed simultaneously with this application entitled "Measurement Of Binding Rate Of A Binding Substance And An Analyte" and claiming priority from British Patent Application No. 0509419.8. However, the sonication apparatus 15 may equally be applied to sonicate a medium 8 in a wide range of other applications, as summarised above. In each case, the medium 8 to be sonicated is arranged in the cuvette 6 and the sonication apparatus 15 is operated as described above. The sonication apparatus 15 may operate at a wide range of frequencies as also summarised above. Change of the operating frequency may require changes in the design of the sonication apparatus 15, eg to change the length of the protruding portions 4 of the sonotrode 2 or to change the materials used, but the fundamental operation remains the same.

The invention claimed is:

1. An apparatus for sonicating a medium comprising:
   a vessel for holding the medium;
   a transducer operable to produce sound waves; and
   a sonotrode coupled to the transducer, the sonotrode comprising a plurality of protruding portions separated by a slit, the plurality of protruding portions being arranged to mechanically hold the vessel.

2. An apparatus according to claim 1, wherein the plurality of protruding portions have facing surfaces which form a recess shaped to mechanically hold the vessel.

3. An apparatus according to claim 2, wherein the recess extends to a lesser depth than the slit.

4. An apparatus according to claim 2, wherein the recess is shaped to conform with the outer surface of the vessel.

5. An apparatus according to claim 2, wherein the recess mechanically holds the vessel by friction.

6. An apparatus according to claim 1, wherein the plurality of protruding portions of the sonotrode are arranged to mechanically hold the vessel on their outer ends.

7. An apparatus according to claim 6, wherein the outer ends of the sonotrode are shaped to conform with the vessel.

8. An apparatus according to claim 1, further comprising a loading arrangement arranged to load the vessel against the protruding portions.

9. An apparatus according to claim 1, wherein the protruding portions have a length of the order of a quarter of the wavelength of the sound waves in the material of the protruding portions.

10. An apparatus according to claim 1, wherein the sonotrode has two said protruding portions separated by the slit.

11. An apparatus according to claim 1, wherein the protruding portions are identical.

12. An apparatus according claim 1, wherein the sonotrode has a base portion from which the protruding portions protrude, the base portion being coupled to the transducer.

13. An apparatus according to claim 1, wherein the sonotrode is formed from a single piece of material.

14. An apparatus according to claim 1, wherein the sonotrode holds the vessel in dry contact.

15. An apparatus according to claim 1, wherein the sonotrode holds the vessel in contact with the vessel without any coupling layers 25 therebetween.

16. An apparatus according to claim 1, wherein vessel is held replaceably by the sonotrode.

17. An apparatus according to claim 1, wherein the transducer is supported by a backing mass providing a reaction to the sound waves.

18. An apparatus according to claim 17, wherein the backing mass is supported by a damper.

19. An apparatus according to claim 1, wherein the vessel is made of a material having an acoustic impedance providing acoustic matching between the sonotrode and the medium.

20. An apparatus according to claim 1, wherein the vessel is made of a plastics material, metal, glass, quartz or silicon.

21. An apparatus according to claim 1, wherein the vessel is made of a thermoplastic olefin polymer of amorphous structure.

22. An apparatus according to claim 1, wherein the resonant frequency of the combination of the sonotrode and the vessel is at least 20 kHz.

23. An apparatus according to claim 1, wherein the resonant frequency of the combination of the sonotrode and the vessel is at most 100 kHz.

24. An apparatus according to claim 1, further comprising a medium held in the vessel and being an assay reagent capable of detecting an analyte.

25. An apparatus according to claim 1, further comprising a drive circuit arranged to provide an oscillatory drive signal for operating the transducer.

26. An apparatus according to claim 25, wherein the drive signal is a pulsed drive signal.

27. An apparatus according to claim 25, wherein the drive signal is oscillatory at a frequency which causes the combination of the sonotrode and the vessel to resonate.

28. An apparatus according to claim 25, wherein the drive circuit includes a detector arranged to monitor the vibration of the apparatus and the drive circuit is arranged to control the oscillatory frequency of the drive signal in response to the output of the detector.

29. An apparatus according to claim 25, wherein the apparatus is arranged to transmit sound waves to the medium with a power of 10 W or less.

30. An apparatus according to claim 1, wherein the apparatus forms part of an immunoassay analyser or a clinical chemistry analyser for sample and reagent processing.

* * * * *